United States Patent [19]

Suzuki et al.

[11] 3,976,702

[45] Aug. 24, 1976

[54] PROCESS FOR PRODUCING ALKYLPHENOLS

[75] Inventors: Takashi Suzuki; Susumu Naito, both of Niigata, Japan

[73] Assignee: Mitsubishi Gas Chemical Company, Inc., Tokyo, Japan

[22] Filed: Mar. 4, 1975

[21] Appl. No.: 555,113

[30] Foreign Application Priority Data

Mar. 4, 1974 Japan.............................. 49-25043

[52] U.S. Cl. .......................... 260/621 R; 260/624 R
[51] Int. Cl.² ........................................ C07C 39/06
[58] Field of Search ........ 260/621 R, 621 G, 624 R, 260/624 C

[56] References Cited
UNITED STATES PATENTS 3,678,104  7/1972  Vesely et al. .................. 260/521 R
3,872,156  3/1975  Bourdin et al. ................ 260/621 R
3,875,247  4/1975  Bourdin et al. ................ 260/621 R

*Primary Examiner*—James O. Thomas, Jr.
*Assistant Examiner*—W. B. Lone

[57] ABSTRACT

This invention relates to a process for producing alkylphenols by oxidation of alkyl-substituted aromatic aldehydes with hydrogen peroxide in the presence of hydrogen fluoride and hydrolysis thereof. More particularly, under the presence of hydrogen fluoride alkyl substituted aromatic aldehydes are oxidized and converted selectively to aromatic alkyl phenol formates by hydrogen peroxide, without converting to corresponding aromatic carboxylic acid. After the completion of the oxidizing reaction, the produced alkyl phenol formates are hydrolyzed to corresponding alkyl phenols at the time of removing the remaining hydrogen fluoride by distillation.

14 Claims, No Drawings

PROCESS FOR PRODUCING ALKYLPHENOLS

BACKGROUND OF THE INVENTION

The alkyl phenols are very useful intermediates in the production of plastics, industrial chemicals, pharmaceuticals, and agricultural chemicals. When alkylphenols are obtained from tar acid or by other synthetic methods, their physical properties of their isomers and homologs resemble closely one another. It is, therefore, disadvantageous to isolate industrially each alkylphenol in a pure state from complicated mixtures such as tar acid which contains a large variety of isomers and homologs. On the other hand, synthetic methods such as the sulfonation-alkali fusion process or the cumene process have also some disadvantages. The former produces many isomers and industrial wastes, and the latter requires a large cost of equipment and is accompanied by many side reactions.

Conversion of carbonyl compounds to esters or carboxylic acids is accomplished generally by Baeyer-Villiger oxidation by the use of a per acid or hydrogen peroxide as oxidizing agents. The per acid is used in the presence of acid catalyst and hydrogen peroxide is used in alkaline medium. Both of these agents are, however, practically inadequate to use, since the per acid is rather expensive and reacts slowly, and hydrogen peroxide reacts less selectively. Moreover, the Baeyer-Villigar reaction does not always give a good yield of phenol esters from aromatic aldehydes, owing to its tendency to be oxidized to carboxylic acids (cf., Japanese published patent application Ser. No. 48-56635). To overcome these disadvantages of hitherto used methods, we have carried out various studies on the synthesis of alkylphenol esters which are readily hydrolyzed to alkylphenols by oxidizing the aromatic aldehydes, and found that alkylphenol esters could be synthesized readily and selectively by oxidizing the aldehydes with hydrogen peroxide in the presence of hydrogen fluoride.

BRIEF SUMMARY OF THE INVENTION

The present invention comprises oxidation of alkyl-substituted aromatic aldehydes of the formula,

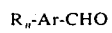

$$R_n\text{-Ar-CHO}$$

wherein R is alkyl group, Ar is a mono- or poly- cyclic aryl group and $n$ is an integer from 1 to 5, with hydrogen peroxide in the presence of hydrogen fluoride. According to the present invention, alkyl-substituted aromatic aldehydes are oxidized to the corresponding alkylphenol esters, the position of the alkyl side chains being unchanged, whereafter the alkylphenol esters thus obtained are hydrolyzed to the corresponding alkylphenols. In the present invention, although the number of carbon atoms in the alkyl radical is not restrictive, a range of from one to four is preferable.

DETAILED DESCRIPTION OF THE INVENTION

Any alkyl-substituted aromatic aldehyde can be used as a starting material in the present invention. Thus, the aldehydes obtained either by formylation or by autooxidation or oxidation with oxidizing agents of substituted aromatic hydrocarbons are of use. Purified alkyl-substituted aromatic aldehydes, prepared by formylation, such as the Gattermann-Koch synthesis, that is, by reaction of aromatic compounds with carbon monoxide in the presence of a Friedel Crafts catalyst, such as anhydrous aluminium chloride or cuprous chloride, are particularly useful. For instance, p-tolu-aldehyde obtained from toluene; 2,4-dimethylbenzaldehyde obtained from m-xylene; 2,5-dimethylbenzaldehyde obtained from p-xylene; 2,4,5- trimethylbenzaldehyde obtained from pseudocumene; and the like, contain less isomeric aldehydes and are suitable for preparing purer alkylphenols.

According to the present invention, the starting alkyl-substituted aromatic aldehydes can be used as a mixture with other aromatic aldehydes or as a solution in saturated or aromatic hydrocarbons.

Anhydrous hydrogen fluoride is favorably employed as the catalyst but moist hydrogen fluoride can also be usable, when reaction condition are suitable, hydrogen fluoride containing less than about 20% of water can be used.

As to the oxidizing agent, good result have been obtained when more concentrated hydrogen peroxide solutions than commercially available (30 wt. % aqueous solution) was used. Hydrogen peroxide solution containing more than about 60 wt. % hydrogen peroxide is preferable, because too much water in the reaction mixture has a tendency to reduce the reaction of the starting materials and to cause side reactions. More preferable results were obtained by using about 90% hydrogen peroxide, as shown in the examples hereinafter set forth.

Although the use of a solvent is not absolutely essential in the present invention, the reaction as described in the presence of an organic solvent is preferable, since the heat produced by the reaction is easily removed in the presence of such solvent. Solvents used in the present invention are preferably compounds containing oxygen atoms in their molecules, such as lower aliphatic alcohols, ethers, esters and carboxylic acids; for instance, methanol, ethanol, diethyl ether, ethyl acetates and acetic acid.

By the use of the above mentioned solvents, crystalline aromatic aldehydes are brought into solution, resulting in a smooth reaction is a homogeneous system and the suppression of side reactions.

According to the present invention, the reaction is conducted at from −50°C to 50°C, preferably at from −20°C to 20°C. The more preferable results were obtained in the range of from 0°C to 10°C. Sometimes the reaction is conducted under pressure to maintain the reaction mixture liquid. Somewhat higher pressure may result by conducting the reaction at higher temperatures.

Although the molar ratio of hydrogen peroxide to the aromatic aldehyde is controlled by various factors, it should be from about 1.05 − 2.00, more preferably 1.05 − 1.30, if one desires to convert more of the aldehyde.

The amount of hydrogen fluoride used varies considerably with the final concentration of water in the reaction system and with the presence or absence of a solvent. Catalitic action of hydrogen fluoride is affected by the ratio between hydrogen fluoride and the compounds including oxygen atoms in the reaction system. A large amount of hydrogen fluoride acidifies the reaction system and catalitic action of the hydrogen fluoride becomes too strong to cause side reactions. The compounds which include oxygen atoms are considered to be bases and weaken the catalitic action of the hydrogen fluoride. When 4 or more mols of hydrogen fluoride to the whole mol of oxygen-containing substances (containing water, hydrogen, peroxide, aromatic aldehyde, reaction products and solvents) are added, side reactions such as condensation and polyhydroxylation of the alkylphenols occur and the desired product is obtained in a very low yield.

On the other hand, when 0.5 or less mole of hydrogen fluoride to the whole mol of oxygen-containing substances is added, its catalytic action is weakened and exhibits unsufficient effects. The most favorable molar ration of hydrogen fluoride to advance the reaction smoothly is 0.8 – 1.20 to the whole mol of substances containing oxygen atoms in their molecules. When a solvent is employed, hydrogen fluoride is added in a molar ration of 3 – 20, preferably 5 – 15, to the aromatic aldehydes. Under these conditions, most of the starting aromatic aldehydes react within 5 – 20 minutes at 0°C to produce the desired alkyl phenol formates.

When the process of this invention is operated by the batch system, either the method in which hydrogen peroxide is added to a mixture of the aromatic aldehyde and hydrogen fluoride or the method in which a mixture of hydrogen fluoride and hydrogen peroxide is added to the aromatic aldehyde can be suitably employed to give good results. According to the present invention, the activity of hydrogen peroxide activated by hydrogen fluoride is so high that the reaction can be completed within a short period of time at such a low temperature as −50°C, resulting in the suppression of side reactions and effective conversion to the alkylphenol esters.

Reaction products produced by the present invention are alkylphenol formates, which are converted to the corresponding alkylphenols by hydrolysis.

The following examples are given for purposes of illustration to aid in understanding the invention, it being understood that the invention is not limited to the specific materials or operating conditions therein disclosed.

EXAMPLE 1

In a 200 cc-autoclave, fitted with a stirrer, were mixed 10g (0.08 mol) of p-tolualdehyde and 30g (0.50 mol) of glacial acetic acid. To the mixture was added 17.2g (0.86 mol) of anhydrous hydrogen fluoride under vigorous stirring and, then, a solution of 4.0g (0.11 mol as $H_2O_2$) of 90 wt.% aqueous hydrogen peroxide in 10g (0.17 mol) of glacial acetic acid was added dropwise over a period of 10 minutes at a temperature of between from 0°C to 10°C while chilling the autoclave by cooling material in the jacket around the autoclave. After stirring the aforesaid mixture for 5 minutes at the same temperature, the contents of the autoclave were transferred to a corrosion-resistant plastic bottle. The bottle was connected with a distillation apparatus and heated on an oil bath to removing the hydrogen fluoride. In this step p-cresol formate was hydrolyzed to p-cresol, and formic acid thus formed was evaporated with the hydrogen fluoride. Gas-chromatographic analysis of a portion of the residue indicated that 95.2 mol% of p-tolualdehyde reacted, and 80.0 mol.% of p-cresol was formed based on the aldehyde reacted.

EXAMPLE 2

By substituting the equimolar amount of ethyl acetate for that of acetic acid in Example 1, 89.2 mol.% of p-tolualdehyde reacted and 78.4 mol.% of p-cresol was formed based on the aldehyde reacted.

EXAMPLE 3

The same autoclave as in Example 1 was charged with a solution of 10g (0.08 mol) of p-tolualdehyde in 82g of an equimolar mixture of hydrogen fluoride and diethyl ether. A mixture of 4.3g (0.11 mol) of 90 wt.% aqueous hydrogen peroxide and 9g of the above-mentioned hydrogen fluoride-diethyl ether mixture was dropped into this solution. The whole mixture was reacted and treated by the same procedure and at the same temperature as in Example 1 : 79.3 mol.% of p-tolualdehyde reacted and 90.2 mol.% of p-cresol was formed based on the aldehyde reacted.

EXAMPLE 4

In the same autoclave as in Example 1 were placed 10.7g (0.09 mol) of p-tolualdehyde, 24g (0.75 mol) of methanol, and 23g (1.15 mol) of anhydrous hydrogen fluoride and, then, a solution of 3.9g (0.10 Mol) of 90 wt.% aqueous hydrogen peroxide in 8g (0.25 mol) of methanol was dropped under the vigorous agitation at +5°C over a period of 10 minutes. The reaction mixture was treated by the same procedure as in Example 1 : 97.8 mol.% of p-tolualdehyde reacted and 81.6 mol.% of p-cresol was obtained based on the aldehyde reacted.

EXAMPLE 5

8g (0.07 mol) of p-tolualdehyde was mixed to 58g of equimolar solution of hydrogen fluoride and methonol. To the mixture 4.5g (0.12 mol as $H_2O_2$) of 90 wt.% aqueous hydrogen peroxide was added slowly and allowed to react at the same temperature as in Example 1. The reaction mixture was treated as in Example 1 : 94.7 mol.% of p-tolualdehyde reacted and 86 mol.% of p-cresol was formed based on the aldehyde reacted.

EXAMPLE 6

By the same procedure as in Example 5, a mixture of 11.7g (0.09 mol) of 2,4-dimethylbenzaldehyde and 4.3g (0.11 mol as $H_2O_2$) of 90 wt.% aqueous hydrogen peroxide was allowed to react with 50g of an equimolar mixture of hydrogen fluoride and methanol.

The reaction mixture was treated as in Example 1 : almost 100% of the aldehyde reacted and 73.6 mol% of 2,4-xylenol was formed based on the aldehyde reacted.

EXAMPLE 7

10g (0.07 mol) of 2,4,5-trimethylbenzaldehyde was mixed to 50g of equimolar solution of hydrogen fluoride and methanol. To the mixture of 3.5g (0.09 mol as $H_2O_2$) of 90 wt.% aqueous hydrogen peroxide was added slowly and allowed to react at the same temperature as in Example 1.

The reaction mixture was treated and analyzed as in Example 1 : almost 100% of the aldehyde reacted and 72.8 mol.% of 2,4,5-trimethylphenol was formed based on the aldehyde reacted.

EXAMPLE 8

10g (0.07 mol) of 4-isopropylbenzaldehyde was mixed to 47g of equimolar solution of hydrogen fluoride and methanol. To the mixture 3.5g (0.09 mol. as $H_2O_2$) wt.% of aqueous hydrogen peroxide was added slowly and allowed to react at the same temperature as in Example 1.

The reaction mixture was treated as in Example 1 : almost 100% of the aldehyde reacted and 78.0 mol.% of 4-isopropyl phenol was formed based on the aldehyde reacted.

EXAMPLE 9

The experiment was conducted with the same amount of materials and by the same procedure as in Example 4, except that aqueous hydrogen peroxide was dropped at from −15°C to −5°C over a period of 15 minutes. After dropping, the mixture was kept quietly for 30 minutes at the same temperature. The reaction mixture was treated by the same procedure as in Example 1 : 94 mol.% of p-tolualdehyde reacted and 74.0 mol.% of p-cresol was obtained based on the aldehyde reacted.

EXAMPLE 10

In the same autoclave as in Example 1 were mixed 12.0g (0.10 mol) of p-tolualdehyde, 12.8g (0.40 mol) of methanol and 9.6g (0.48 mol) of anhydrous hydrogen fluoride and, then, solution of 4.1g (0.11 mol as $H_2O_2$) of 90 wt.% aqueous hydrogen peroxide was dropped under the controlled temperature from 0°C to 10°C. After dropping, the mixture was kept quietly for 20 minutes at the same temperature. The reaction mixture was treated by the same procedure as in Example 1 : 95 mol.% of p-tolualdehyde reacted and 78.0 mol.% of p-cresol was obtained based on the p-tolualdehyde reacted.

EXAMPLE 11

In the same autoclave as in Example 1 were mixed 10.7g (0.09 mol.) of p-tolualdehyde, 24g (0.75 mol) of methanol and 25.4g (1.27 mol) of anhydrous hydrogen fluoride and, then, a solution of 5.4g (0.10 mol as $H_2O_2$) of 60 wt.% aqueous hydrogen peroxide in 8g (0.25 mol) of methanol was dropped and reacted under the same procedure as in Example 4. The reaction mixture was treated by the same procedure as in Example 1 : 93 mol.% of p-tolualdehyde reacted and 80.3 mol.% of p-cresol was obtained based on the p-tolualdehyde reacted.

EXAMPLE 12 – 16

To the mixture of p-tolualdehyde, ethanol, and unhydrous hydrogen fluoride was dropped 90 wt.% aqueous hydrogen peroxide at from 0°C to 5°C, and reacted for 20 minutes. The reaction mixture was treated the same procedure as in Example 1. The amount of the materials used and the results are shown in the table 1 as follows:

Table 1

| Example No. | p-tolualdehyde | | ethanol | | 90 wt.% $H_2O_2$ | | hydrogen fluoride | | HF/total amount of substances containing oxygen atoms | p-tolualdehyde reacted % | p-cresol produced based on p-tolualdehyde reacted. % |
|---|---|---|---|---|---|---|---|---|---|---|---|
| | g | mol | g | mol | g | mol | g | mol | | | |
| 12 | 15.0 | 0.13 | 23.8 | 0.51 | 5.1 | 0.14 | 23.8 | 1.19 | 1.45 | 94.7 | 74.2 |
| 13 | 10.0 | 0.08 | 28.2 | 0.61 | 3.9 | 0.10 | 18.4 | 0.92 | 1.14 | 93.0 | 85.6 |
| 14 | 10.2 | 0.9 | 33.7 | 0.73 | 3.6 | 0.10 | 17.9 | 0.89 | 0.95 | 94.6 | 90.5 |
| 15 | 10.0 | 0.08 | 40.8 | 0.88 | 3.7 | 0.10 | 17.7 | 0.88 | 0.81 | 90.2 | 88.5 |
| 16 | 9.9 | 0.08 | 62.1 | 1.35 | 3.8 | 0.10 | 18.0 | 0.90 | 0.58 | 87.1 | 78.2 |

COMPARATIVE EXAMPLE I

By substituting an equimolar amount of benzaldehyde for that of dimethylbenzaldehyde in Example 6, 95.4 mol.% of the aldehyde reacted, but merely 7.4 mol.% of phenol was obtained based on benzaldehyde reacted.

COMPARATIVE EXAMPLE II

By substituting an equimolar mixture of hydrogen chloride and methanol for the mixture of hydrogen fluoride and methanol in Example 5, 94.8 mol.% of p-tolualdehyde reacted, but merely 34.6 mol.% of p-cresol was obtained based on the aldehyde reacted.

What we claim is:

1. A process for preparing alkylphenols, comprising the steps of subjecting an alkyl-substituted aromatic aldehyde of the formula;

$R_nArCHO$ 

wherein R represents linear or branched alkyl radicals containing 1 to 4 carbon atoms, Ar is a phenyl radical and $n$ is an integer from 1 to 5, to oxidation to a corresponding alkylphenol formate in the presence of hydrogen fluoride and aqueous hydrogen peroxide solution containing at least 30% by weight of hydrogen peroxide in an amount of from about 1.05 to 2.00 mol as $H_2O_2$ to one mol of starting aldehyde, at a temperature of about −50°C to 50°C and hydrolyzing the alkyl phenyl formate thus produced to the corresponding alkyl phenol in the presence of water.

2. A process as claimed in claim 1, wherein the alkyl-substituted aromatic aldehyde is reacted in an organic solvent selected from the group consisting of saturated lower aliphatic alcohols, saturated carboxylic acids, saturated ethers and saturated alkyl esters.

3. A process as claimed in claim 1, wherein the hydrogen fluoride is present in an amount of from about 0.5 to 4 mol per mol (taken together) of the substances in the reaction mixture containing oxygen atoms in their molecules, including water, hydrogen peroxide, aromatic aldehyde, reaction products and solvents.

4. A process as claimed in claim 1, wherein the hydrogen fluoride is present in an amount of from about 0.8 to 1.20 mol per mol (taken together) of the substances in the reaction mixture containing oxygen atoms in their molecules, including water, hydrogen peroxide, aromatic aldehyde, reaction products and solvents.

5. A process for preparing alkylphenols, comprising the steps of subjecting an alkyl-substituted aromatic aldehyde of the formula, RnArCHO wherein, R represents linear or branched alkyl radicals containing 1 to 4 carbon atoms, Ar is a phenyl radical and n is a integer from 1 to 5, to oxidation to a corresponding alkylphenol formate in a solution comprising:
   a. hydrogen fluoride in an amount of from about 3 to 20 mol per mol of alkyl-substituted aromatic aldehyde;
   b. aqueous hydrogen peroxide solution containing at least 30% by weight of hydrogen peroxide in an amount of from about 1.05 to 2.00 mol as $H_2O_2$ per mol of starting aldehyde; and
   c. an organic solvent selected from the group consisting of saturated aliphatic alcohols, saturated carboxylic acids, saturated alkyl ethers and saturated alkyl esters,
at a temperature range from about −50°C to 50°C, and hydrolyzing the alkyl phenyl formate thus produced to the corresponding alkyl phenol in the presence of water.

6. A process as claimed in claim 5, wherein the solvent is selected from methanol, ethanol, diethyl ether, ethyl acetate and acetic acid.

7. A process as claimed in claim 5, wherein from 5 to 15 mol of hydrogen fluoride to one mol of alkyl-substituted aromatic aldehyde, is used.

8. A process as claimed in claim 5, wherein from 1.05 to 1.30 mol as $H_2O_2$ of aqueous hydrogen peroxide to one mol of starting aldehyde is used as the oxidizing agent.

9. A process as claimed in claim 5, wherein aqueous hydrogen peroxide containing at least 60 wt.% of $H_2O_2$, is used.

10. A process as claimed in claim 5, wherein aqueous hydrogen peroxide containing at least about 90 wt.% of $H_2O_2$, is used.

11. A process as claimed in claim 5, wherein anhydrous hydrogen fluoride is used.

12. A process as claimed in claim 5, wherein the oxidation is conducted at a temperature from about −20°C to 20°C.

13. A process as claimed in claim 5, wherein the oxidation is conducted at a temperature from about 0°C to 10°C.

14. A method according to claim 5, wherein the alkyl-substituted aromatic aldehyde is selected from the group consisting of p-tolu-aldehyde; 2,4-dimethylbenzaldehyde; 2,5-dimethylbenzaldehyde; 2,4,5-trimethylbenzaldehyde; and 4-isopropylbenzaldehyde.

* * * * *